(12) United States Patent  (10) Patent No.: US 8,524,508 B2
Lennon et al.  (45) Date of Patent: Sep. 3, 2013

(54) METHODS OF TREATING NEUROMYELITIS OPTICA (NMO)

(75) Inventors: Vanda A. Lennon, Rochester, MN (US); Thomas J Kryzer, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 855 days.

(21) Appl. No.: 12/105,755

(22) Filed: Apr. 18, 2008

(65) Prior Publication Data

US 2009/0143710 A1  Jun. 4, 2009

Related U.S. Application Data

(60) Division of application No. 11/457,685, filed on Jul. 14, 2006, now Pat. No. 7,947,254, which is a continuation of application No. 10/723,180, filed on Nov. 25, 2003, now Pat. No. 7,101,679.

(51) Int. Cl.
*G01N 33/53* (2006.01)

(52) U.S. Cl.
USPC ........... 436/547; 436/543; 436/544; 436/545; 436/546; 436/548

(58) Field of Classification Search
None
See application file for complete search history.

(56) References Cited

U.S. PATENT DOCUMENTS

| | | | |
|---|---|---|---|
| 4,708,713 A | 11/1987 | Lentz | |
| 5,214,136 A | 5/1993 | Lin et al. | |
| 5,218,105 A | 6/1993 | Cook et al. | |
| 5,258,503 A | 11/1993 | Yokohari et al. | |
| 5,386,734 A | 2/1995 | Pusinelli | |
| 5,614,192 A | 3/1997 | Vandenbark | |
| 5,976,872 A | 11/1999 | Tao et al. | |
| 6,066,726 A | 5/2000 | Farb et al. | |
| 6,409,696 B1 | 6/2002 | Toavs et al. | |
| 6,409,726 B1 | 6/2002 | Ellman et al. | |
| 6,905,827 B2 | 6/2005 | Wohlgemuth et al. | |
| 7,026,121 B1 | 4/2006 | Wohlgemuth et al. | |
| 7,947,254 B2 | 5/2011 | Lennon et al. | |
| 2002/0037273 A1 | 3/2002 | Cummins et al. | |
| 2003/0072737 A1 | 4/2003 | Brines et al. | |
| 2004/0014087 A1 | 1/2004 | Hodgson et al. | |
| 2004/0048253 A1 | 3/2004 | Panzer et al. | |
| 2004/0073377 A1 | 4/2004 | Pittman et al. | |
| 2004/0115629 A1 | 6/2004 | Panzer et al. | |
| 2012/0219969 A1 | 8/2012 | Lennon et al. | |

OTHER PUBLICATIONS

GenBank Accession No. AAB26957 dated Nov. 22, 1996.
GenBank Accession No. AAB26958 dated Nov. 22, 1996.
GenBank Accession No. AAG17964 dated Oct. 3, 2000.
GenBank Accession No. BC022286 dated Jun. 29, 2004.
GenBank Accession No. I39178 dated Jun. 20, 2000.
GenBank Accession No. NM_001650 dated Oct. 28, 2004.
GenBank Accession No. NM_004028 dated Oct. 28, 2004.
GenBank Accession No. U63622 dated Nov. 22, 1996.
GenBank Accession No. U63623 dated Nov. 22, 1996.
Haase and Schmidt, "Detection of brain-specific autoantibodies to myelin oligodendrocyte glycoprotein, S100β and myelin basic protein in patients with Devic's neuromyelitis optica," *Neurosci. Lett.*, 2001, 307(2):131-133.
Habibaghahi, "Anticardiolipin Antibody in Patients with Multiple sclerosis," *Shiraz E-Medical J.*, 3(3) at http://www.sums.ac.ir/~semj/vol3/may2002/rACAinMS.htm printed from internet on Feb. 18, 2003.
Harlow and Lane, "Antibodies," A Laboratory Manual, 1988, Cold Spring Harbor Laboratory, Chapter 5, p. 76.
Jambou et al., "Circulating regulatory anti-T cell receptor antibodies in patients with myasthenia gravis," *J. Clin. Invest.*, 2003, 112:265-274.
Luck et al., "Single Amino Acid Substitutions in Recombinant Bovine Prolactin That Markedly Reduce Its Mitogenic Activity in Nb2 Cell Cultures," *Mol. Endocrinol.*, 1991, 5(12):1880-1886.
Mackay, "Tolerance and autoimmunity," *British Med. J.*, 2000, 321:93-96.
Matsumoto et al., "Successful TCR-Based Immunotherapy for Autoimmune Myocarditis with DNA Vaccines After Rapid Identification of Pathogenic TCR," *J. Immunol.*, 2000, 164:2248-2254.
Miyagishi et al., "Two cases of recurrent optic neuritis (OPN) and acute transverse myelopathy (ATM) with associated anticardiolipin antibodies," *Clin. Neurol.*, 1992, 32(10):1121-1124, English-language Abstract.
Neely et al., "Syntrophin-dependent expression and localization of Aquaporin-4 water channel protein," *Proc. Natl. Acad. Sci. USA*, 2001, 98(24):14108-14113.
Parker et al., "Scheme for Ranking Potential HLA-A2 Binding Peptides Based on Independent Binding of Individual Peptide Side-Chains," *J. Immunol.*, 1994, 152:163-175.
Robin et al., "Anti-Myelin Basic Protein Antibody in Experimental Allergic Optic Neuritis and Encephalomyelitis,"*Opthalmic Res.*, 1985, 17(3):174-180.
Sakuma et al., "Optic-spinal form of multiple sclerosis and anti-thyroid autoantibodies," *J. Neurol.*, 1999, 246(6):449-453.
Schwartz, "Direct Visualization of Antigen-Specific Cytotoxic T Cells—A New Insight into Immune Defenses," *N. Engl. J. Med.*, 1998, 339(15):1076-1078.
Sellebjerg et al., "Anti-Myelin Basic Protein and Anti-Proteolipid Protein Antibody-Secreting Cells in the Cerebrospinal Fluid of Patients With Acute Optic Neuritis," *Arch. Neurol.*, 1994, 51(10):1032-1036.
Soderstrom et al., "Optic neuritis and multiple sclerosis: Anti-MBP and anti-MBP peptide antibody-secreting cells are accumulated in CSF," *Neurology*, 1993, 43(6):1215-1222.
Southwood et al., "Several Common HLA-DR Types Share Largely Overlapping Peptide Binding Repertoires," *J. Immunol.*, 1998, 160:3363-3373.
Tumani et al., "Acute optic neuritis: combined immunological markers and magnetic resonance imaging predict subsequent development of multiple sclerosis," *J. Neurol. Sci.*, 1998, 155(1):44-49.
Verkman et al., "Role of water channels in fluid transport studied by phenotype analysis of aquaporin knockout mice," *Exp. Physiol.*, 2000, 85S:233S-241S.

(Continued)

*Primary Examiner* — Chang-Yu Wang
(74) *Attorney, Agent, or Firm* — Fish & Richardson P.C.

(57) ABSTRACT

The present invention provides for methods and materials for diagnosing and treating neuromyelitis optica (NMO).

11 Claims, 4 Drawing Sheets

(56) References Cited

OTHER PUBLICATIONS

Vizuete et al., "Differential upregulation of aquaporin-4 mRNA expression in reactive astrocytes after brain injury: potential role in brain edema," *Neurobiol. Dis.*, 1999, 6:245-258.

Bowie et al., "Deciphering the Message in Protein Sequences: Tolerance to Amino Acid Substitutions," *Science*, 1990, 247:1306-1310.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Bio.*, 1990, 111:2129-2138.

Jung et al., "Molecular characterization of an aquaporin cDNA from brain: Candidate osmoreceptor and regulator of water balance," *PNAS*, 1994, 91:13052-13056.

Pawson et al., "Assembly of Cell Regulatory Systems Through Proteins Interaction Domains," *Science*, 2003, 300:445-452.

Kim et al., 2013, "Clinical efficacy of plasmapheresis in patients with neuromyelitis optica spectrum disorders and effects on circulating anti-aquaporin-4 antibody levels," *J. Clin. Neurol.*, 9:36-42.

Varrin-Doyer et al., 2012, "Aquaporin 4-specific T cells in neuromyelitis optica exhibit a Th17 bias and recognize Clostridium ABC transporter," *Ann. Neurol.*, 72:53-64.

Kim et al., 2013, "Utility of aquaporin-4 antibody assay in patients with neuromyelitis optica spectrum disorders," *Mult. Scler.*, e-pub PMID 23329699.

Figure 1

| Serum # | Result/ Comment | Cerebellar Cortex | | | | | Midbrain | | | Kidney |
|---|---|---|---|---|---|---|---|---|---|---|
| | | Pia | WM | GL | ML | Other | Pia | Subpia | Other | |
| ___ | | | | | | | | | | |
| ___ | | | | | | | | | | |
| ___ | | | | | | | | | | |
| ___ | | | | | | | | | | |
| ___ | | | | | | | | | | |
| ___ | | | | | | | | | | |
| ___ | | | | | | | | | | |
| ___ | | | | | | | | | | |

Score Sheet NMO-IgG exp:_____  Assay: _/_/_  Read: _/_/_  By:____

Figure 2-1

```
AccI        GT'mk_AC (0 Err) - 2 Fragment(s)
    243        909

ApaI        G_GGCC'C (0 Err) - 2 Fragment(s)
    402        750

BamHI       G'GATC_C (0 Err) - 2 Fragment(s)
    200        952

EcoRI       G'AATT_C (0 Err) - 2 Fragment(s)
    343        809

HindIII     A'AGCT_T (0 Err) - 2 Fragment(s)
    135        1017

NciI        CC's_GG (0 Err) - 2 Fragment(s)
    196        956

NcoI        C'CATG_G (0 Err) - 4 Fragment(s)
    60         135        288        669

PstI        C_TGCA'G (0 Err) - 3 Fragment(s)
    337        366        449

PvuII       CAG'CTG (0 Err) - 2 Fragment(s)
    570        582

SalI        G'TCGA_C (0 Err) - 2 Fragment(s)
    242        910
```

== Linear Map of Sequence:

```
  1    ggggcaggcaatgagagctgcactctggctggggaaggcatgagtgacagacccacagca    60
       ccccgtccgttactctcgacgtgagaccgacccctccgtactcactgtctgggtgtcgt
        ^    *    ^    *    ^    *    ^    *    ^    *    ^    *

61    aggcggtggggtaagtgtggacctttgtgtaccagagagaacatcatggtggctttcaaa   120
       tccgccaccccattcacacctggaaacacatggtctctcttgtagtaccaccgaaagttt
        ^    *    ^    *    ^    *    ^    *    ^    *    ^    *

HindIII
                  \
121    ggggtctggactcaagcttctggaaagcagtcacagcggaatttctggccatgcttatt   180
       ccccagacctgagttcgaaagacctttcgtcagtgtcgccttaaagaccggtacgaataa
        ^    *    ^    *    ^    *    ^    *    ^    *    ^    *

BamHI
                       \
181    tttgttctcctcagcctgggatccaccatcaactggggtggaacagaaaagcctttaccg   240
       aaacaagaggagtcggaccctaggtggtagttgaccccaccttgtctttcggaaatggc
        ^    *    ^    *    ^    *    ^    *    ^    *    ^    *

SalI
```

Figure 2-2

```
         AccI                                          NcoI
         \\                                             \
241   gtcgacatggttctcatctcccttt gctttggactcagcattgcaaccatggtgcagtgc   300
      cagctgtaccaagagtagagggaaacgaaacctgagtcgtaacgttggtaccacgtcacg
        ^    *    ^    *    ^    *    ^    *    ^    *    ^    *

PstI      NcoI
                                             \          \
301   tttggccatatcagcggtggccacatcaaccctgcagtgactgtggccatggtgtgcacc   360
      aaaccggtatagtcgccaccggtgtagttgggacgtcactgacaccggtaccacacgtgg
        ^    *    ^    *    ^    *    ^    *    ^    *    ^    *

361   aggaagatcagcatcgccaagtctgtcttctacatcgcagcccagtgcctgggggccatc   420
      tccttctagtcgtagcggttcagacagaagatgtagcgtcgggtcacggaccccggtag
        ^    *    ^    *    ^    *    ^    *    ^    *    ^    *

421   attggagcaggaatcctctatctggtcacacctcccagtgtggtgggaggcctgggagtc   480
      taacctcgtccttaggagatagaccagtgtggagggtcacaccaccctccggaccctcag
        ^    *    ^    *    ^    *    ^    *    ^    *    ^    *

NcoI
       \
481   accatggttcatggaaatcttaccgctggtcatggtctcctggttgagttgataatcaca   540
      tggtaccaagtacctttagaatggcgaccagtaccagaggaccaactcaactattagtgt
        ^    *    ^    *    ^    *    ^    *    ^    *    ^    *

PvuII
                               \
541   tttcaattggtgtttactatctttgcagctgtgattccaaacggactgatgtcactggc   600
      aaagttaaccacaaatgatagaaacggtcgacactaaggtttgcctgactacagtgaccg
        ^    *    ^    *    ^    *    ^    *    ^    *    ^    *

601   tcaatagctttagcaattggattttctgttgcaattggacatttatttgcaatcaattat   660
      agttatcgaaatcgttaacctaaaagacaacgttaacctgtaaataaacgttagttaata
        ^    *    ^    *    ^    *    ^    *    ^    *    ^    *

PstI
                                         \
661   actggtgccagcatgaatcccgcccgatcctttggacctgcagttatcatgggaaattgg   720
      tgaccacggtcgtacttagggcgggctaggaaacctggacgtcaatagtaccctttaacc
        ^    *    ^    *    ^    *    ^    *    ^    *    ^    *

ApaI
                         \
721   gaaaaccattggatatattgggttgggcccatcataggagctgtcctcgctggtggcctt   780
      cttttggtaacctatataacccaacccgggtagtatcctcgacaggagcgaccaccggaa
        ^    *    ^    *    ^    *    ^    *    ^    *    ^    *

EcoRI
                      \
781   tatgagtatgtcttctgtccagatgttgaattcaaacgtcgttttaaagaagccttcagc   840
      atactcatacagaagacaggtctacaacttaagtttgcagcaaaatttcttcggaagtcg
        ^    *    ^    *    ^    *    ^    *    ^    *    ^    *
```

Figure 2-3

```
 841   aaagctgcccagcaaacaaaaggaagctacatggaggtggaggacaacaggagtcaggta   900
       tttcgacgggtcgtttgttttccttcgatgtacctccacctcctgttgtcctcagtccat
          ^    *    ^    *    ^    *    ^    *    ^    *    ^    *

NciI
                                                             \
 901   gagacggatgacctgattctaaaacctggagtggtgcatgtgattgacgttgaccgggga   960
       ctctgcctactggactaagattttggacctcaccacgtacactaactgcaactggcccct
          ^    *    ^    *    ^    *    ^    *    ^    *    ^    *

961   gaggagaagaaggggaaagaccaatctggagaggtattgtcttcagtatgactagaagat   1020
       ctcctcttcttccccttTctggttagacctctccataacagaagtcatactgatcttcta
          ^    *    ^    *    ^    *    ^    *    ^    *    ^    *

1021   cgcactgaaagcagacaagactccttagaactgtcctcagatttccttccacccattaag   1080
       gcgtgactttcgtctgttctgaggaatcttgacaggagtctaaaggaaggtgggtaattc
          ^    *    ^    *    ^    *    ^    *    ^    *    ^    *

1081   gaaacagatttgttataaattagaaatgtgcaggtttgttgtttcatgtcatattactca   1140
       ctttgtctaaacaatatttaatctttacacgtccaaacaacaaagtacagtataatgagt
          ^    *    ^    *    ^    *    ^    *    ^    *    ^    *

1141   gtctaaacaata                                                   1200
       cagatttgttat
          ^    *    ^    *    ^    *    ^    *    ^    *    ^    *

==------------------- End of Analysis -------------------==
```

METHODS OF TREATING NEUROMYELITIS OPTICA (NMO)

CROSS REFERENCE TO RELATED APPLICATIONS

This application is a Divisional of and claims the benefit of priority under 35 U.S.C. §120 to U.S. application Ser. No. 11/457,685 having a filing date of Jul. 14, 2006 now U.S. Pat. No. 7,947,254, which is a Continuation of and claims the benefit of priority under 35 U.S.C. §120 to U.S. application Ser. No. 10/723,180 having a filing date of Nov. 25, 2003, now issued as U.S. Pat. No. 7,101,679. The disclosures of the prior applications are incorporated by reference in their entirety.

TECHNICAL FIELD

This invention relates generally to neurological disorders, and more particularly, to an autoantibody marker for neuromyelitis optica and the Asian opticospinal form of multiple sclerosis (MS).

BACKGROUND

Neuromyelitis optica (NMO) is a neurological disorder also known as Devic's syndrome in Western countries and as opticopinal multiple sclerosis in Asia. NMO is regarded as a severe variant of multiple sclerosis (MS), and accounts for 30% of MS cases occurring in Asians. In North America, non-Caucasians represent a higher frequency of patients with NMO than the frequency of those with classical MS. The characteristic inflammatory demyelinating lesions of NMO selectively and repeatedly affect the optic nerves and the spinal cord, thereby causing both blindness and paralysis.

SUMMARY

A specific marker has been identified in serum and cerebrospinal fluid of patients with neuromyelitis optica (NMO) and the Asian opticospinal form of MS. The presence of an NMO-specific antibody can be used to distinguish NMO from MS, and also can be used to diagnose NMO at an early stage of the disease before all clinical criteria are fulfilled, thus justifying early initiation of NMO-appropriate immunosuppressive therapy.

In one aspect, the invention provides methods of detecting the presence or absence of a NMO-specific autoantibody in a biological sample from an individual. Such a method includes contacting the biological sample with a NMO antigenic polypeptide or fragment thereof, where the NMO antigenic polypeptide is aquaporin-4; and detecting the presence or absence of binding of the NMO antigenic polypeptide to the NMO-specific autoantibody in the biological sample. In one embodiment, the NMO antigenic polypeptide is a recombinantly-expressed NMO antigenic polypeptide. In another embodiment, the NMO-specific polypeptide is in a solid tissue selected from the group consisting of brain, spinal cord, optic nerve, kidney, or stomach.

For example, the presence of the NMO-specific autoantibody in the biological sample can be associated with vision impairment, weakness, numbness, spasms or abnormal or painful sensations, and/or loss of bladder and/or bowel control in the individual. In addition, the presence of the NMO-specific autoantibody is generally associated with NMO in the individual. Representative biological sample is selected from the group consisting of blood, serum, plasma, and cerebrospinal fluid.

In another aspect, the invention provides methods of detecting the presence or absence of a NMO antigenic polypeptide in a biological sample from an individual. Such a method includes contacting the biological sample with an anti-NMO antigen antibody, where the NMO antigen is aquaporin-4; and detecting binding of the anti-NMO antigen antibody to the biological sample, wherein binding is indicative of the presence of the NMO antigenic polypeptide in the biological sample. Generally, the presence of the NMO antigenic polypeptide in the biological sample is indicative of NMO in the individual. Such an individual may be partially or completely blind. Representative biological samples include blood, serum, plasma, cerebrospinal fluid, brain biopsy, and spinal cord biopsy.

In another aspect, the invention provides an article of manufacture including a NMO antigenic polypeptide and instructions for using the NMO antigenic polypeptide to detect an anti-NMO antigen autoantibody in an individual. The NMO antigenic polypeptide is aquaporin-4. Such an article of manufacture can be used to diagnose NMO in the individual. In an embodiment, the article of manufacture can further include a monoclonal antibody having specific binding affinity for a NMO antigenic polypeptide.

In yet another aspect, the invention provides methods of treating an individual having NMO. Such methods include withdrawing a body fluid from the individual, wherein the body fluid contains one or more autoantibodies that bind to aquaporin-4; removing a substantial portion of the autoantibodies from the body fluid; and returning the body fluid to the subject.

In still another aspect, the invention provides methods of treating an individual having NMO by administering a NMO antigenic polypeptide to the individual. The NMO antigenic polypeptide is aquaporin-4. Generally, administration is by a method such as oral, intravenous, and parenteral administration.

In another aspect, the invention provides methods of treating an individual having NMO by administering a nucleic acid encoding a NMO antigenic polypeptide to the individual. The NMO antigenic polypeptide is aquaporin-4.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods and examples are illustrative only and not intended to be limiting. All publications, patent applications, patents and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 is a score sheet used to evaluate the immunohistochemical staining pattern and intensity of tissues contacted with serum from an individual.

FIG. 2 is a restriction map of a human aquaporin-4 nucleic acid.

Like reference symbols in the various drawings indicate like elements.

DETAILED DESCRIPTION

A specific IgG autoantibody marker has been identified in serum and cerebrospinal fluid of patients with neuromyelitis optica (NMO) and Asian opticospinal MS (NMO is used synonymously in this application to refer to both NMO and Asian opticospinal MS). In addition, this autoantibody can be found in patients with a spectrum of inflammatory disorders involving spinal cord, optic nerve, and more rarely, brainstem or other regions of the brain, that were not hitherto recognized as being related to NMO.

The presence of an NMO-specific antibody can be used to diagnose NMO at an early stage of the disease before all clinical criteria are fulfilled, thus justifying early initiation of NMO-appropriate immunosuppressant therapy, and further can be used to distinguish NMO from MS. Detecting NMO-specific antibody also can provide a quantifiable biomarker for monitoring disease progression and response to therapy. The pattern of immunostaining also can be used to classify disorders related to NMO, including variants of multiple sclerosis, isolated optic neuritides, certain myelopathies and "optico-spinal" accompaniments of systemic lupus erythematosus and Sjogren's syndrome. In addition, the identification of an antibody associated with NMO provides a valuable IgG tool for developing animal models (e.g., by passive transfer of NMO-specific antibodies or active immunization with NMO antigenic polypeptides or DNA vaccines encoding such antigenic polypeptides) to investigate the pathogenesis of NMO lesions and to test potential new therapies for NMO.

NMO Antigenic Polypeptides and NMO-Specific Antibodies

The present invention provides for methods of detecting NMO-specific autoantibodies in an individual using NMO antigenic polypeptides. Individuals for whom the methods of the invention might be used typically present with vision impairment and/or tingling, numbness, weakness, limb spasms, loss of bladder and/or bowel control, or other neurological symptoms of unknown origin. The method of the invention is based on an association between the abnormal neurological symptoms and the presence of the NMO-specific autoantibodies in the individual.

NMO antigenic polypeptides include to one or more epitopic sites. Epitopes of NMO antigenic polypeptides that are pertinent to T-cell activation and suppression are also provided by the invention. Computer algorithms are available for predicting binding epitopes, e.g., MHC-I and MHC-II binding epitopes. See, for example, bimas.dcrt.nih.gov:80/molbio/hla_bind/ on the World Wide Web (Parker et al., *J. Immunol.*, 152:163 (1994); Southwood et al., *J. Immunol.*, 160:3363 (1998)). The term "characteristic" in this context means that the epitopic site allows immunologic detection of NMO-specific antibody in sera with reasonable assurance. Usually, it is desirable that the epitopic site be antigenically distinct from other closely related antigens (e.g., other members of a family of polypeptides). A representative antigenic fragment can include, for example, the extracellular domain of a membrane-bound protein.

The NMO antigenic polypeptides may be obtained from cells (e.g., transfected host cells) expressing a nucleic acid, or the polypeptides may be synthetic. A DNA molecule encoding a NMO antigenic polypeptide or fragment thereof may itself be natural or synthetic, with natural genes obtainable from human tissues by conventional techniques.

The NMO antigenic polypeptides can be obtained in a substantially pure form. With respect to polypeptides, "purified" refers to a polypeptide that constitutes the major component in a mixture of components, e.g., 50% or more, 60% or more, 70% or more, 80% or more, 90% or more, or 95% or more, by weight. Purified polypeptides are typically obtained by purification from an organism that makes the polypeptide, although chemical synthesis is also feasible. The polypeptides may be purified by routine protein purification methods, including affinity chromatography or immunosorbant affinity column.

NMO antigenic polypeptides of the present invention may be used with or without modification for the detection of NMO-specific autoantibodies. Frequently, polypeptides are labeled by either covalently or non-covalently combining the polypeptide with a second substance that provides for detectable signal. A wide variety of labels and conjugation techniques are known in the art and are reported extensively in both the scientific and patent literature. Some of the labels include radioisotopes, enzymes, substrates, cofactors, inhibitors, fluorescers, chemiluminescers, magnetic particles, and the like.

NMO antigenic polypeptides prepared as described above can be used in various immunological techniques for detecting NMO-specific autoantibodies in biological samples, such as from serum and cerebrospinal fluid. Depending on the nature of the sample, either or both immunoassays and immunocytochemical staining techniques may be used. Enzyme-linked immunosorbent assays (ELISA), Western blot, and radioimmunoassays are routine methods in the art and may be used to detect the presence of NMO-specific autoantibodies in sera.

Further provided by the invention are kits containing one or more NMO antigenic polypeptides. The kit may further include a second substance that provides for detectable signal. A kit typically also includes directions for using the NMO antigenic polypeptide and/or for practicing a method of the invention (i.e., detecting NMO-specific autoantibodies in a biological sample).

The present invention also provides for methods of detecting NMO antigenic polypeptides in a biological sample from an individual. The method describes an association between the presence of abnormal levels or pattern of expression of the NMO antigenic polypeptide, the subsequently produced NMO-specific autoantibody, and the resulting NMO in the individuals. This test is most widely applicable to those individuals who present with neurological symptoms or blindness, and those individuals who are suspected of having MS or NMO. Detection of a polypeptide is typically performed using an antibody, referred to herein as an anti-NMO antigen antibody to distinguish such animal- or recombinantly-generated antibodies from NMO-specific autoantibodies produced by an individual's immune system. The invention also provides for an antibody, including a monoclonal antibody with specific binding affinity for NMO antigenic polypeptides.

Once a sufficient quantity of NMO antigenic polypeptides has been obtained, monoclonal or polyclonal anti-NMO antigen antibodies having specific binding affinity for the NMO antigenic polypeptide may be produced by techniques well known to those of ordinary skill in this art. As used herein, anti-NMO antigen antibodies having "specific binding affinity" for NMO antigenic polypeptides are defined as those antibodies that bind NMO antigenic polypeptides but that do not bind other polypeptides, for example, other members of a family of polypeptides. As used herein, "anti-NMO antigen antibody" refers to whole antibodies of any class, i.e., IgG, IgA, IgM or any other known class, and also includes portions or fragments of whole antibodies (e.g., Fab or (Fab)$_2$ fragments) having the desired specific binding affinity, an engineered single chain Fv molecule, or a chimeric molecule, e.g., an antibody that contains the binding specificity of one antibody (e.g., of murine origin) and the remaining portions of another antibody (e.g., of human origin).

Anti-NMO antigen antibodies of the present invention may be used with or without modification for the detection of NMO antigenic polypeptides. Anti-NMO antigen antibodies can be labeled either directly or indirectly, and a wide variety of labels, including radioisotopes, enzymes, substrates, cofactors, inhibitors, fluorescers, chemiluminescers and magnetic particles, and conjugation techniques are known and are reported extensively in both the scientific and patent literature.

Anti-NMO antigen antibodies prepared as described above can be used in various immunological techniques for detecting NMO antigenic polypeptides in a biological sample. A "biological sample," as used herein, is generally a sample from an individual. Non-limiting examples of biological samples include blood, serum, plasma, or cerebrospinal fluid. Additionally, solid tissues, for example, spinal cord or brain biopsies may be used. The use of antibodies in protein binding assays is well established. Depending on the nature of the sample, immunoassays (e.g., radioimmunoassays) and/or immunohistochemical/immunocytochemical staining techniques may be used. Liquid phase immunoassays (e.g., competitive inhibition radioimmunoassays) or solid phase immunoassays (e.g., antigen-capture or Western blot analysis) can also be used to detect NMO antigenic polypeptides in a biological sample. Additionally, enzyme-linked immunosorbent assays (ELISA) are routinely practiced in the art, and may be used for detecting the presence of NMO antigenic polypeptides in a biological sample.

Numerous competitive and non-competitive protein-binding assays have been described in the scientific and patent literature, and a large number of such assays are commercially available. An example of one such competitive assay for detecting the presence of a NMO antigenic polypeptide in a biological sample such as serum, comprises: contacting a NMO antigenic polypeptide (either labeled or unlabeled) with an anti-NMO antigen antibody (either labeled or unlabeled) and the biological sample. The NMO antigenic polypeptide may be, for example, attached to a solid surface. Using known amounts of NMO antigenic polypeptide and labeled anti-NMO antigen antibody to generate a standard binding curve, the relative amount of NMO antigenic polypeptide in a biological sample can be determined.

Further provided by the invention is a kit containing anti-NMO antigen antibodies having binding affinity for NMO antigenic polypeptides or fragments thereof. The kit may also include NMO antigenic polypeptides or fragments thereof to be used as binding controls or to generate a standardized quantitative curve. The kit may further include a second substance that provides for detectable label. A kit typically includes directions for using an anti-NMO antigen antibody and/or practicing a method of the invention (i.e., detecting NMO antigenic polypeptides in a biological sample).

Also provided by this invention is an anti-NMO antigen antibody having specific binding affinity for NMO antigenic polypeptides conjugated to a detectable marker. Suitable detectable markers include, but are not limited to, enzymes, radioisotopes, dyes and biotin. This invention further provides an anti-NMO antigen antibody having specific binding affinity for NMO antigenic polypeptides conjugated to an imaging agent. Suitable imaging agents include, but are not limited to, radioisotopes, such as $^{32}$P, $^{99}$Tc, $^{111}$In and $^{131}$I.

Methods of Treating NMO

Further provided by the invention are methods of treating an individual having NMO. Treatment of NMO requires modulating the neurological symptoms in the individual resulting from NMO-specific immune mechanisms. Methods of treating an individual with NMO include, without limitation, apheresis and T cell receptor-based immunotherapy.

Methods and extracorporeal systems for apheresis (i.e., the process of withdrawing blood from an individual, removing components from the blood, and returning the blood, or blood depleted of one or more components, to the individual) are known in the art (see, for example, U.S. Pat. Nos. 4,708,713; 5,258,503; 5,386,734; and 6,409,696). The invention provides a method of removing NMO-specific autoantibodies from a body fluid of an individual. The method involves withdrawing a body fluid from a subject; removing a substantial portion of NMO-specific autoantibodies from the fluid; and returning the fluid to the subject. Antibodies removed can be of any class, e.g., IgG (such as IgG1, IgG2, IgG3, IgG4), IgM, IgD, IgA, or IgE antibodies.

As used herein, a "substantial portion" means removing at least 20% (e.g., at least: 20%; 30%; 40%; 50%; 60%; 65%; 70%; 75%; 80%; 85%; 90%; 93%; 95%; 96%; 97%; 98%; 99%; 99.5%; 99.8%; or even 100%) of the NMO-specific autoantibodies that were present in the body fluid prior to removal. The body fluid can be blood plasma or any other body fluid, e.g., lymph or cerebrospinal fluid. According to the methods of the invention, depleting NMO-specific autoantibodies from individuals with NMO will result in a decrease in symptoms.

Removal of NMO-specific autoantibodies is generally performed by contacting a body fluid with a NMO antigenic polypeptide. The NMO antigenic polypeptide can be bound to a solid support. Such solid supports can be, without limitation, membranes, fibers, spherical beads, or granules and can be made with a water-insoluble, preferably porous, biocompatible material, e.g., organic polymers such as agarose, dextran, and polyacrylamide, or inorganic porous materials such as porous glass or porous silica gel. Such materials are suitable or can be adapted (e.g., derivatized with appropriate chemical groups) for attachment of a NMO antigenic polypeptide.

When the body fluid is blood, the plasma and/or white blood cells can be separated from red blood cells (e.g., erythrocytes) and the red blood cells can be returned to the individual with or without white blood cells. Usually, the blood cells are returned to the individual with artificial rather than their original blood plasma. The "replacement fluid" (e.g., physiological saline) can be administered to the individual after removal of the fluid. Alternatively, the NMO-specific autoantibodies can be selectively removed from the blood plasma in the course of apheresis and the blood cells can be mixed with the NMO-specific autoantibody-depleted plasma and then re-infused as a mixture into the individual.

The system can be a continuous one in which, for example, blood is pumped out of a blood vessel (e.g., an artery or a vein) passed over a solid support derivatized with NMO antigenic polypeptides and pumped directly back into a blood vessel of the subject. As in non-continuous systems, blood cells can be separated from plasma prior to passing of the plasma over the solid support.

Methods of T cell receptor therapy are known in the art. See, for example, U.S. Pat. No. 5,614,192; Matsumoto et al., 2000, *J. Immunol.*, 164:2248-54; and Mackay, 2000, *British Med. J.*, 321:93-6. Monoclonal or polyclonal antibodies having specific binding affinity for the antigen(s) expressed by the NMO antigen-receptor or other marker on the T cell population responsible for inducing and maintaining the production of NMO-specific autoantibodies can be used to deplete or suppress one or more pathogenic T cells. CDR3 spectratyping of T cell receptors can be used to identify autoimmune disease-associated T cell receptors (Matsumoto et al., supra; and Jambou et al., 2003, *J. Clin. Invest.*, 112: 254-74). In addition, activation of T cells can be inhibited in an individual by administering a cytokine or an antibody having specific binding affinity for a cytokine. For example, to decrease a Th1-type immune response, a cytokine such as interleukin (IL)-4, IL-10, or IL-13, or an antibody specific for a cytokine such as IL-12 or interferon (IFN)-γ can be administered to an individual. Similarly, to inhibit a Th2-type immune response, a cytokine such as IL-12 or IFN-γ or an antibody specific for IL-4, IL-10, or IL-13 can be administered to an individual.

In addition, a therapeutic method of the invention includes administering an effective amount of a pharmaceutical composition (e.g., a NMO antigenic polypeptide or a nucleic acid such as an antisense oligonucleotide or a nucleic acid encoding an NMO antigenic polypeptide) to the individual. An effective amount is an amount of NMO antigenic polypeptide that deviates the individual's NMO antigenic polypeptide-mediated immune response, thereby modulating a neurological disorder in the individual. As used herein, "modulating" a neurological disorder can refer to reducing the severity of one or more symptoms, eliminating all symptoms, or any level of symptoms therebetween.

An "antisense oligonucleotide" is an oligonucleotide that can specifically hybridize to a target nucleic acid, and the modulation of expression of a target nucleic acid by an antisense oligonucleotide is generally referred to as "antisense technology." The term "hybridization," as used herein with respect to antisense technology, refers to hydrogen bonding, which can be Watson-Crick, Hoogsteen, or reversed Hoogsteen hydrogen bonding, between complementary regions of the target nucleic acid and the antisense oligonucleotide. "Specifically hybridizable" is used to indicate a sufficient degree of complementarity or precise pairing such that stable and specific binding occurs between the antisense oligonucleotide and the target nucleic acid. It is understood in the art that the sequence of an antisense oligonucleotide need not be 100% complementary to that of its target nucleic acid to be specifically hybridizable.

The specific hybridization of an antisense oligonucleotide with its target nucleic acid can interfere with the normal function of the target nucleic acid. For a target DNA nucleic acid, antisense technology can disrupt replication and transcription. For a target RNA nucleic acid, antisense technology can disrupt, for example, translocation of the RNA to the site of protein translation, splicing of the RNA to yield one or more mRNA species, catalytic activity of the RNA, and translation of protein from the RNA. The overall effect of such interference with target nucleic acid function is, in the case of a nucleic acid encoding a NMO antigenic polypeptide, modulation of disease symptoms associated with NMO. In the context of the present invention, antisense technology can be used to decrease expression of a gene encoding a NMO antigenic polypeptide (e.g., due to inhibition of transcription) and/or decrease the cellular levels of the NMO antigenic polypeptide (e.g., due to inhibition of translation).

Preferred target sites for antisense oligonucleotides have included the regions encompassing the translation initiation or termination codon of the open reading frame (ORF) of the target gene. In addition, the open reading frame has been targeted effectively in antisense technology, as have the 5' and 3' untranslated regions. Furthermore, antisense oligonucleotides have been successfully directed at intron regions and intron-exon junction regions. Additionally, multiple antisense oligonucleotides can be used that each specifically hybridize to a different region of a target gene.

Antisense oligonucleotides useful in methods of the invention are generally from about 10 to about 50 nucleotides in length (e.g., 12 to 40, 14 to 30, or 15 to 25 nucleotides in length), but can be longer or shorter so long as the antisense oligonucleotide is able to modulate the symptoms associated with NMO. As used herein, antisense oligonucleotides include oligonucleotides composed of naturally occurring nucleobases, sugars, and covalent internucleoside (backbone) linkages, as well as oligonucleotides containing modified backbones (e.g., substituted sugar moieties) or non-natural internucleoside linkages. Antisense oligonucleotides also include oligonucleotide analogs such as peptide nucleic acids (PNAs) or chimeric oligonucleotides. Further, antisense oligonucleotides of the invention can be modified by chemical linkage to one or more moieties or conjugates that enhance the activity, cellular distribution or cellular uptake of the oligonucleotide. See, for example, U.S. Pat. Nos. 5,218,105 and 5,214,136.

The ability of an antisense oligonucleotide to inhibit expression and/or production of a NMO antigenic polypeptide can be assessed, for example, by measuring levels of mRNA or protein in an individual before and after treatment. Methods for measuring mRNA and protein levels in tissues or biological samples are well known in the art.

NMO antigenic polypeptides also can be delivered in vivo by administering a vector appropriately expressing a nucleic acid encoding a NMO antigenic polypeptide to the individual. Vectors for delivering nucleic acids that encode biologically useful proteins (e.g., a NMO antigenic polypeptide) to an individual are known in the art. Current virus-based nucleic acid delivery vectors are typically derived from animal viruses, such as adenovirus, adeno-associated virus, retroviruses, lentiviruses, vaccinia virus, herpes viruses, and bovine papilloma virus. Vectors for nucleic acid delivery usually have been genetically modified such that the native tropism and pathogenicity of the virus have been altered or removed. The genome of a virus also can be modified to increase its infectivity and to accommodate packaging of nucleic acids encoding, for example, a biologically useful protein. In addition, non-viral vectors and methods of using such vectors for nucleic acid delivery are known to those of skill in the art.

As used herein, "administering" refers to a method of delivering a composition of the invention (e.g., a NMO antigenic polypeptide, an antisense oligonucleotide that hybridizes specifically to a portion of the nucleic acid encoding an NMO antigenic polypeptide, or a nucleic acid encoding a NMO antigenic polypeptide) to the patient. Such methods are well known to those skilled in the art and include, but are not limited to, oral, nasal, intravenous, intramuscular, intraperitoneal, subcutaneous, intrathecal, intradermal, or topical administration. The route of administration can depend on a variety of factors, such as the therapeutic goals. Compositions of the invention may be administered on a continuous or an intermittent basis. Methods for formulating and subsequently administering therapeutic compositions are well known to those skilled in the art. See, for example, Remington, 2000, *The Science and Practice of Pharmacy*, 20th Ed., Gennaro & Gennaro, eds., Lippincott, Williams & Wilkins. The dose administered will depend on many factors, including the mode of administration and the formulation. Typically, the amount in a single dose is an amount that effectively reduces the level of NMO antigenic polypeptides or NMO-specific autoantibodies in an individual without exacerbating the disease symptoms.

In addition, a NMO antigenic polypeptide within the scope of the invention additionally can contain a pharmaceutically acceptable carrier for in vivo administration to an individual, including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers can also include physiologically acceptable aqueous vehicles (e.g., physiological saline or artificial cerebral-spinal fluid) or other known carriers appropriate to specific routes of administration. Additional compounds can be included with a NMO antigenic polypeptide, such as steroids, mucolytic agents, anti-inflammatory agents, immunosuppressants, dilators, vasoconstrictors, or combinations thereof. Preservatives, flavorings, and other additives such as, for example, anti-microbials, anti-oxidants, chelating agents, inert gases, and the like may also be present.

Methods to deliver a composition to the brain are known in the art. For example, a composition of the invention can be modified by attaching a ligand (e.g., an antibody or antibody fragment) that recognizes a brain-specific or neuron-specific receptor. In addition, methods of enhancing transport of molecules across the blood-brain barrier are known, and take advantage of passive diffusion (e.g., using electromagnetic fields, nitric oxide donors or sodium caprate) or receptor-mediated endocytosis (e.g., attachment of the virus particle to, for example, an anti-transferrin antibody or to putrescine). Expression of a viral vector carrying nucleic acid sequence encoding a NMO antigenic polypeptide also can be targeted using brain-specific or neuron-specific promoter and/or transcriptional regulatory elements (see, for example, U.S. Pat. No. 5,976,872 or 6,066,726). A particularly useful promoter for neuronal-specific expression of a nucleic acid encoding a NMO antigenic polypeptide is a prion promoter.

Also provided by this invention is a method of imaging NMO antigenic polypeptide-expressing cells in a patient. The method comprises administering to the patient an effective amount of an anti-NMO antigen antibody having specific binding affinity for a NMO antigenic polypeptide labeled with an imaging agent, for example, $^{32}P$, $^{99}Tc$, $^{111}In$ or $^{131}I$, to bind to a NMO antigenic polypeptide released from, or accessible in, cells, and detecting any complex so formed. As is well known to those of ordinary skill in the art, a suitable amount of an anti-NMO antigen antibody is any amount that is effective to image cells, for example, about 0.1 mCi to about 50.0 mCi. In addition, an effective amount of the an anti-NMO antigen antibody may be an amount from about 0.01 mg to about 100 mg. Suitable methods of administering the imaging agent are as described above an can be targeted (e.g., to the brain) as described above. Methods of imaging are dependent upon the agent used and are well known to those of skill in this art.

Also provided by the invention is a method of enumerating or isolating NMO antigenic polypeptide-specific T-lymphocytes in an individual. This method may be used, for example, to monitor an individual's immune response or for immunotherapy using NMO antigenic polypeptide-specific cytotoxic T-cells. The method comprises contacting a biological sample containing lymphocytes with tetrameric soluble class I or class II major histocompatibility complex (MHC) bearing identical NMO antigenic polypeptide fragments. Linker molecules such as avidin and biotin are used to produce the NMO antigenic polypeptide-MHC tetrameric complex, which can subsequently be labeled with an indicator molecule such that those T-cells that recognize the NMO antigenic polypeptide-MHC tetrameric complex are enumerated or isolated (e.g., using FACS analysis). See, for example, Schwartz, 1998, *New England J. Med.,* 339:1076-8, and references therein.

Nucleic Acids and Constructs

Experimental evidence as disclosed herein suggests that the NMO antigenic polypeptide is aquaporin-4. The term "aquaporin-4" refers to a member of the aquaporin family. The aquaporin family has 10 known members. Aquaporin-4 is expressed in the astrocytic foot process membrane contacting capillaries in the central nervous system, and also in the basolateral membrane of renal distal collecting tubules. Examples of a nucleotide sequence encoding a human aquaporin-4 polypeptide are shown in GenBank Accession Nos. U63622 and U63623. The predicted amino acid sequences of representative human aquaporin-4 polypeptides are shown in GenBank Accession Nos. AAG17964, AAB26957, AAB26958, and I39178. Nucleic acid and amino acid sequences encoding aquaporin-4 from other organisms (e.g., *Mus musculus, Bos Taurus, Rattus norvegicus*, and *Ovis aries*) can be found by searching the GenBank database (at ncbi.nlm.nih.gov on the World Wide Web) using "aquaporin-4" as the search word.

As used herein, nucleic acid refers to RNA or DNA. As used herein with respect to nucleic acids, "isolated" refers to (i) a nucleic acid sequence encoding part or all of the human aquaporin-4 polypeptide, but free of coding sequences that normally flank one or both sides of the nucleic acid sequences encoding aquaporin-4 in the human genome; or (ii) a nucleic acid incorporated into a vector or into the genomic DNA of an organism such that the resulting molecule is not identical to any naturally-occurring vector or genomic DNA.

In another aspect, the invention includes fragments of the human aquaporin-4 nucleic acid and polypeptide. As used herein, fragments refer to nucleic acids or polypeptides corresponding to less than the entire aquaporin-4 sequence. Nucleic acid fragments may include those fragments of about 100 nucleotides in length as well as fragments that are several hundred nucleotides in length of GenBank Accession Nos. U63622 or U63623; or fragments of GenBank Accession Nos. U63622 or U63623 of about 10 to 50 nucleotides in length. Fragments provided by the invention include, for example, nucleotides 166-266, 283-306, 404-1104, 575-925, 648-698, 712-747, and 891-906 of GenBank Accession Nos. U63622 or U63623. Such fragments may, for example, encode an aquaporin-4 antigenic polypeptide fragment, or have utility as hybridization probes or amplification primers.

FIG. 2 shows the relative position of various restriction enzyme sites within a human aquaporin-4 nucleic acid sequence that, by way of example, define positions, which, in various combinations, can be used to generate useful nucleic acid fragments. Given the nucleotide sequence of a human aquaporin-4 polypeptide, virtually any nucleic acid fragment can be generated by known means (e.g., restriction enzyme digestion, the polymerase chain reaction) and, if so desired, expressed to produce the corresponding polypeptide fragment. Alternatively, the human aquaporin-4 polypeptide can be cleaved (e.g., proteolytically) to directly generate polypeptide fragments.

A human aquaporin-4 nucleic acid or nucleic acid fragment may have a sequence that deviates from that shown in GenBank Accession Nos. U63622 or U63623. For example, a nucleic acid sequence can have at least 80% sequence identity to the nucleotide sequence shown in GenBank Accession Nos. U63622 and U63623. In some embodiments, the nucleic acid sequence can have at least 85% sequence identity, 90% sequence identity, 95% sequence identity, or at least 99% sequence identity to GenBank Accession Nos. U63622 and U63623. See, for example, GenBank Accession Nos. BC022286, NM_004028, and NM_001650 for variant nucleic acid sequences of aquaporin-4.

Percent sequence identity is calculated by determining the number of matched positions in aligned nucleic acid or polypeptide sequences, dividing the number of matched positions by the total number of aligned nucleotides or amino acids, respectively, and multiplying by 100. A matched position refers to a position in which identical nucleotides or amino acids occur at the same position in aligned sequences. The total number of aligned nucleotides or amino acids refers to the minimum number of aquaporin-4 nucleotides or amino acids that are necessary to align the second sequence, and does not include alignment (e.g., forced alignment) with non-aquaporin-4 sequences, such as those fused to aquaporin-4. The total number of aligned nucleotides or amino acids may correspond to the entire aquaporin-4 sequence or may correspond to fragments of the full-length aquaporin-4 sequence as defined herein.

Sequences can be aligned using the using the algorithm described by Altschul et al. (1997, *Nucleic Acids Res.*, 25:3389-3402) as incorporated into BLAST (basic local alignment search tool) programs, available at ncbi.nhn.nih.gov on the World Wide Web. BLAST searches or alignments can be performed to determine percent sequence identity between an aquaporin-4 nucleic acid molecule and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between an aquaporin-4 sequence and another sequence, the default parameters of the respective programs are used.

A nucleic acid encoding a human aquaporin-4 polypeptide may be obtained from, for example, a cDNA library made from a human cell line, or can be obtained by other means, including, but not limited to, the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach & Dveksler, Eds., Cold Spring Harbor Laboratory Press, 1995. Generally, sequence information from the ends of the region of interest or beyond is employed to design oligonucleotide primers that are identical or similar in sequence to opposite strands of the template to be amplified.

Human aquaporin-4 nucleic acids can be detected by, for example, a variety of hybridization techniques. Hybridization between nucleic acid molecules is discussed in detail in Sambrook et al. (1989, *Molecular Cloning: A Laboratory Manual*, 2$^{nd}$ Ed., Cold Spring Harbor Laboratory Press, Cold Spring Harbor, N.Y.; Sections 7.37-7.57, 9.47-9.57, 11.7-11.8, and 11.45-11.57).

For oligonucleotide probes less than about 100 nucleotides, Sambrook et al. discloses suitable Southern blot conditions in Sections 11.45-11.46. The Tm between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47-9.52). Hybridizations with an oligonucleotide greater than 100 nucleotides generally are performed 15-25° C. below the Tm. The Tm between a sequence greater than 100 nucleotides in length and a second sequence can be calculated using the formula provided in Sections 9.50-9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations can be performed, where appropriate, under moderate or high stringency conditions. Such conditions are described, for example, in Sambrook et al. section 11.45-11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a first target nucleic acid but not to a second target nucleic acid if hybridization to the first nucleic acid is at least 5-fold (e.g., at least 6-fold, 7-fold, 8-fold, 9-fold, 10-fold, 20-fold, 50-fold, or 100-fold) greater than hybridization to the second nucleic acid. The amount of hybridization can be quantitated directly on a membrane or from an autoradiograph using, for example, a PhosphorImager or a Densitometer (Molecular Dynamics, Sunnyvale, Calif.).

The present invention further includes vectors containing a human aquaporin-4 nucleic acid (see, for example, GenBank Accession Nos. U63622 and U63623) or the complements thereof, aquaporin-4 nucleic acid fragments or the complements thereof, and those nucleic acids having at least 80% sequence identity to an aquaporin-4 nucleic acid or fragments generated therefrom (or the complements thereof).

Cloning vectors suitable for use in the present invention are commercially available and used routinely by those of ordinary skill. Vectors of the invention may additionally comprise elements necessary for expression operably linked to a human aquaporin-4 nucleic acid sequence. "Elements necessary for expression" include promoter sequences, and additionally may include regulatory elements, such as enhancer sequences, response elements or inducible elements that modulate expression of the human aquaporin-4 nucleic acid sequence. As used herein, "operably linked" refers to positioning of a promoter and/or other regulatory element(s) in a construct relative to the human aquaporin-4 nucleic acid sequences in such a way as to direct or regulate expression of the aquaporin-4 nucleic acid. Such constructs are commercially available (e.g., expression vectors) and/or produced by recombinant DNA technology methods routine in the art. The choice of expression systems depends upon several factors, including, but not limited to, replication efficiency, selectability, inducibility, targeting, the level of expression desired, ease of recovery and the ability of the host to perform post-translational modifications.

As used herein, the term "host" or "host cell" is meant to include not only prokaryotes, such as E. coli, but also eukaryotes, such as yeast, insect, plant and animal cells. Animal cells include, for example, COS cells and HeLa cells. A host cell can be transformed or transfected with a DNA molecule (e.g., a vector) using any of the techniques commonly known to those of ordinary skill in this art, such as calcium phosphate or lithium acetate precipitation, electroporation, lipofection or particle bombardment. Host cells containing a vector of the present invention may be used for purposes such as propagating the vector, producing human aquaporin-4 nucleic acid (e.g., DNA, RNA, antisense RNA), or expressing the human aquaporin-4 polypeptide or fragments thereof.

In another aspect of the invention, methods of producing aquaporin-4 polypeptides are provided. Methods of producing aquaporin-4 polypeptides include, but are not limited to, culturing host cells containing an aquaporin-4 expression vector under conditions permissive for expression of aquaporin-4, and recovering the aquaporin-4 polypeptides. Methods of culturing bacteria and recovering expressed polypeptides are well known to those of ordinary skill in this art.

Additionally, nucleic acids of the present invention may be detected by methods such as Southern or Northern blot analysis (i.e., hybridization), PCR, or in situ hybridization analysis. Aquaporin-4 proteins are typically detected by immunocytochemistry in transfected cell lines or by sodium dodecyl sulphate (SDS)-polyacrylamide gel electrophoresis followed by Coomassie Blue-staining or Western blot analysis using antibodies (monoclonal or polyclonal) that have specific binding affinity for a human aquaporin-4 polypeptide.

The invention will be further described in the following examples, which do not limit the scope of the invention described in the claims.

EXAMPLES

Example 1

Serum Preabsorption

To minimize non-specific staining, each patient's serum was preabsorbed with liver antigens by mixing 40 mg of commercial guinea pig tissue powder (Sigma Chemical Co., St. Louis, Mo.) with 10 µL of serum diluted in 590 µL of phosphate-buffered saline (PBS) containing 1% bovine serum albumen. After gently mixing for 1 hour at room temperature, insoluble residue was removed by centrifuging (20, 800×g for 10 minutes). Fresh liver powder (40 mg) was then immediately added to the serum supernatant, and the process was repeated an additional two times for a total of 3 consecutive absorptions.

Example 2

Substrate Preparation

A frozen composite block of three normal mammalian tissues (e.g., mouse brain (both cerebellum and midbrain), stomach and kidney) was cryosectioned (4 µthickness) onto individual wells of an 8-well microscope slide. These slides were purchased as a custom product (from MeDiCa, Encinitas, Calif.) and stored at −70° C. in individual sealed packets containing desiccant. Before opening for use, each packet was equilibrated at room temperature. Chilled detergent (1% CHAPS in PBS) was applied to each section and aspirated after 4 minutes. After 3 washes in chilled PBS (each wash was for 5 minutes on a shaker), chilled 10% phosphate-buffered formalin was applied and aspirated after 4 minutes. After 3 more 5-minute washes in chilled PBS, PBS containing 10% normal goat serum (at room temperature) was applied and aspirated after 60 minutes.

Example 3

Immunostaining

Absorbed, diluted patient and control sera (40 µL volumes) were applied individually to wells containing the above-described treated tissue sections. After 40 minutes at room temperature, each well was washed thoroughly with chilled PBS. A commercial fluorochrome-conjugated IgG specific for human IgG (e.g., fluoresceinated goat anti-human IgG, Southern Biotechnology Assoc., Inc., Birmingham, Ala.) is then applied at the appropriate dilution. After 35 minutes at room temperature, the wells were washed thoroughly in chilled PBS and a glass coverslip (#1 thickness) was applied to each slide with mounting medium containing an anti-fade reagent. The slides were evaluated by fluorescence microscopy (20× objective) for the characteristic NMO pattern of tissue-bound IgG.

In the central nervous system (CNS), the NMO antigen was localized on the abluminal face of capillaries in the cerebellar cortex, midbrain and spinal cord; in optic nerve, the NMO antigen was associated with pia and astrocytic processes in the region of capillaries amongst axon columns. In optimally treated sections of CNS tissues, immunofluorescence confocal microscopy suggested that the NMO antigen is a component of the blood-brain barrier. Immunoreactivity was inherent in the glia limitans of the astrocytic-pial junction, extending into the Virchow-Robin space to the smallest capillaries in white matter and gray matter. Dual immunostaining with affinity-purified antibodies of defined specificity revealed co-localization of the NMO antigen with aquaporin-4, a mercurial-insensitive water channel protein constituent of the blood-brain-barrier. The NMO antigen is not detectable in sections of spleen or liver parenchyma but, like aquaporin-4, it is prominently associated with basolateral membranes of distal collecting tubules in the kidney, and with basal elements of deep gastric mucosal epithelium.

By using a limiting dilution of NMO-IgG in a competitive inhibition immunofluorescence assay, enrichment of immunoreactivity was demonstrated in the crude membrane fraction prepared from homogenized rat brain by differential centrifugation. This fraction potently quenched the NMO-IgG immunofluorescence pattern. Fractions containing tissue debris and nuclei were relatively depleted of immunoreactivity, and cytosol did not absorb the reactivity of NMO-IgG. The crude membrane fraction's immunoreactivity resisted extraction in a 2% solution of the non-ionic detergent CHAPS. This observation led to the discovery that treatment of tissue sections with 1% CHAPS for 4 minutes, before or after fixation for 4 minutes in 10% phosphate buffered formalin, preserved tissue morphology and enhanced the accessibility of NMO epitopes to IgG in serum of 70% of patients with a clinical diagnosis of NMO.

Although not bound by any particular theory, the resistance of the NMO antigen to detergent extraction is consistent with the proposed tethering of the cytoplasmic C-terminus of aquaporin-4 to a PDZ-domain of the scaffolding adapter protein α-syntrophin, which is a component of the dystrophin protein complex (Neely et al., *PNAS* 98:14108, 2001).

Example 4

Interpreting Immunohistochemical Staining Results

Table 1 shows the characteristic features that were evaluated in each of the indicated tissues:

TABLE 1

| | |
|---|---|
| cerebellum | pia, white matter matrix and capillaries, granular layer capillaries, and molecular layer capillaries |
| midbrain | pia, subpia, white matter and capillaries |
| kidney | distal collecting tubules (binds NMO-IgG most avidly) |
| stomach | basal epithelium of deep mucosa (binds NMO-IgG least avidly) |

The staining intensity of each characteristic is graded on a formal score sheet (FIG. 1), using the following scoring system:

negative: − or ±/−
faint positive, may be equivocal: ±
definite positive, strong: ±/+, + or 2+

A positive result requires a minimum of a '±' score to be assigned to the kidney's distal collecting tubules and to cerebellar or midbrain pia or capillaries.

The presence and intensity of any nuclear, cytoplasmic, membranous or extracellular matrix staining that may potentially interfere with NMO-IgG interpretation is noted. In particular, staining in any of the tissues indicated in Table 2 is noted for each tissue section examined.

TABLE 2

| | |
|---|---|
| cerebellum/ midbrain | neurons, myelin, arteriolar smooth muscle |
| stomach | mucosal epithelium, enteric neurons, and smooth muscle |
| kidney | cortical tubules, glomeruli, arterioles, sympathetic nerves, other |

Example 5

Clinical Application

Serum was analyzed from patients classified as "definite" NMO, the Asian opticospinal form of MS, or classical MS by clinical, imaging and spinal fluid criteria, and from control patients, for autoantibodies that might bind selectively to CNS tissues. The experiments described herein demonstrate the value of seropositivity for discriminating NMO from the classic form of multiple sclerosis (MS). Sera (coded at testing) were from patients with definite NMO using diagnostic criteria of varying grades of stringency (n=45), patients with classic MS (n=19), patients deemed to be at high risk for MNO (bilateral optic neuritis or single or recurrent attacks of longitudinally extensive myelitis; each associated with negative brain MRI, i.e., not fulfilling stringent criteria for "definite" NMO classification) (n=35), and patients ultimately diagnosed with MS but initially presenting with optic neuritis or myelitis (n=22). Indirect immunofluorescence was performed with a standard composite substrate of mouse brain, gut and kidney; sera were preabsorbed with liver extract as described above in Example 1.

IgG in 33 of 45 patients (73%) with NMO yielded a distinctive staining pattern ("NMO-IgG") associated with capillaries throughout the cerebellar cortex and midbrain, and with pia and a subpial "mesh" (prominent in midbrain). The capillary pattern was not seen in gut mucosa, kidney, or liver, and NMO-IgG was not noted in any control disease group. Sera from 16 out of 35 patients (46%) that were at high risk for NMO yielded the staining pattern distinctive for NMO-IgG. None of the 19 patients diagnosed with classic MS had detectable staining patterns of NMO-IgG, while sera from 2 out of the 22 patients (9%) that presented with optic neuritis/myelitis possessed the NMO-IgG.

Additionally, a NMO-IgG was identified incidentally in 14 patients amongst 85 thousand whose sera were submitted to Mayo Clinic's Neuroimmunology Laboratory for blinded paraneoplastic autoantibody testing on a service basis. Their subsequently-obtained histories revealed that 3 fulfilled clinical criteria for the diagnosis of NMO, 9 were classified as high risk for NMO (7 had longitudinally extensive myelitis and 2 had recurrent optic neuritis), 1 had new onset myelopathy, and 1 had unclassified steroid-responsive CNS inflammatory disorder.

These results indicated that the NMO-IgG autoantibody is the first specific biological marker of NMO and is able to distinguish NMO from MS.

Example 6

Western Blot

A GST fusion protein containing recombinant rat aquaporin-4 (C terminal residues 249-323; Alamone Labs, Jerusalem, Israel) was electrophoresed in a 10% polyacrylamide gel in standard Laemmli SDS buffer containing β-mercaptoethanol, and a Western blot was performed using NMO patients' and immune rabbit's serum as a positive control to determine whether or not the patients' IgG would bind to the 38 kDa GST-aquaporin-4 fusion protein. The blot was contacted with human sera (1:50 dilution), which included 4 NMO patients, 3 normal persons, 1 control myelopathy, 2 patients with classic MS, and 3 patients with miscellaneous neuropsychiatric disorders. Serum from the four NMO patients and from the immune rabbit, but none of the serum from the control patients or from patients exhibiting the other disorders, bound the 38 kDa aquaporin-4 fusion protein.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of removing autoantibodies against aquaporin-4 from an individual having neuromyelitis optica (NMO), said method comprising:
   withdrawing a body fluid sample from the individual, wherein the body fluid sample contains one or more autoantibodies that bind to aquaporin-4;
   removing, from the body fluid sample, at least 20% of the autoantibodies that bind to aquaporin-4 that are present in the body fluid sample using an antigenic aquaporin-4 polypeptide to produce an autoantibody-depleted body fluid sample; and
   returning the autoantibody-depleted body fluid sample to the subject, wherein said removing step and said returning step are performed using apheresis, wherein the body fluid sample is selected from the group consisting of plasma and cerebrospinal fluid.

2. The method of claim 1, wherein the aquaporin-4 polypeptide is human.

3. The method of claim 1, wherein the aquaporin-4 polypeptide is bound to a solid support.

4. The method of claim 1, wherein at least 30% of the autoantibodies that bind to aquaporin-4 in the body fluid sample are removed from the body fluid sample.

5. The method of claim 1, wherein at least 50% of the autoantibodies that bind to aquaporin-4 in the body fluid sample are removed from the body fluid sample.

6. The method of claim 1, wherein said apheresis is non-continuous.

7. A method of removing T cells from an individual having neuromyelitis optica (NMO), said method comprising:
   withdrawing a body fluid from the individual, wherein the body fluid contains one or more T cells responsible for inducing the production of autoantibodies that bind to aquaporin-4;
   removing T cells from the body fluid using an antibody directed toward an aquaporin-4 marker on said T cells; and
   returning the body fluid to the subject, wherein said removing step and said returning step are performed using apheresis, wherein the body fluid is selected from the group consisting of plasma and cerebrospinal fluid.

8. The method of claim 7, wherein the antibody is a polyclonal antibody.

9. The method of claim 7, wherein the antibody is a monoclonal antibody.

10. The method of claim 7, wherein the antibody directed toward said aquaporin-4 marker is bound to a solid support.

11. The method of claim 7, wherein said apheresis is non-continuous.

\* \* \* \* \*

SEQUENCE LISTING

<160> NUMBER OF SEQ ID NOS: 1

<210> SEQ ID NO 1
<211> LENGTH: 1152
<212> TYPE: DNA
<213> ORGANISM: Homo sapiens

<400> SEQUENCE: 1

```
ggggcaggca atgagagctg cactctggct ggggaaggca tgagtgacag acccacagca      60
aggcggtggg gtaagtgtgg acctttgtgt accagagaga acatcatggt ggctttcaaa     120
ggggtctgga ctcaagcttt ctggaaagca gtcacagcgg aatttctggc catgcttatt     180
tttgttctcc tcagcctggg atccaccatc aactggggtg gaacagaaaa gcctttaccg     240
gtcgacatgg ttctcatctc cctttgcttt ggactcagca ttgcaaccat ggtgcagtgc     300
tttgccata tcagcggtgg ccacatcaac cctgcagtga ctgtggccat ggtgtgcacc      360
aggaagatca gcatcgccaa gtctgtcttc tacatcgcag cccagtgcct ggggccatc      420
attggagcag gaatcctcta tctggtcaca cctcccagtg tggtgggagg cctgggagtc     480
accatggttc atggaaatct taccgctggt catggtctcc tggttgagtt gataatcaca     540
tttcaattgg tgtttactat cttttgccagc tgtgattcca aacggactga tgtcactggc    600
tcaatagctt tagcaattgg attttctgtt gcaattggac atttatttgc aatcaattat    660
actggtgcca gcatgaatcc cgcccgatcc tttggacctg cagttatcat gggaaattgg    720
gaaaaccatt ggatatattg ggttgggccc atcataggag ctgtcctcgc tggtggcctt    780
tatgagtatg tcttctgtcc agatgttgaa ttcaaacgtc gttttaaaga agccttcagc   840
aaagctgccc agcaaacaaa aggaagctac atggaggtgg aggacaacag gagtcaggta    900
gagacggatg acctgattct aaaacctgga gtggtgcatg tgattgacgt tgaccgggga    960
gaggagaaga aggggaaaga ccaatctgga gaggtattgt cttcagtatg actagaagat    1020
cgcactgaaa gcagacaaga ctccttagaa ctgtcctcag atttccttcc acccattaag    1080
gaaacagatt tgttataaat tagaaatgtg caggtttgtt gtttcatgtc atattactca    1140
gtctaaacaa ta                                                        1152
```